(12) United States Patent
Ikeda et al.

(10) Patent No.: US 6,340,428 B1
(45) Date of Patent: Jan. 22, 2002

(54) DEVICE AND METHOD FOR DETERMINING THE CONCENTRATION OF A SUBSTRATE

(75) Inventors: Shin Ikeda, Katano; Toshihiko Yoshioka; Shiro Nankai, both of Hirakata, all of (JP)

(73) Assignee: Matsushita Electric Industrial Co., Inc., Osaka (JP)

( * ) Notice: Subject to any disclaimer, the term of this patent is extended or adjusted under 35 U.S.C. 154(b) by 0 days.

(21) Appl. No.: 09/424,715

(22) PCT Filed: Mar. 31, 1999

(86) PCT No.: PCT/JP99/01706

§ 371 Date: Nov. 29, 1999

§ 102(e) Date: Nov. 29, 1999

(87) PCT Pub. No.: WO99/51974

PCT Pub. Date: Oct. 14, 1999

(30) Foreign Application Priority Data

Apr. 2, 1998 (JP) .......................................... 10/089740
Jun. 19, 1998 (JP) .......................................... 10/172766

(51) Int. Cl.$^7$ ............................................... G01N 27/26
(52) U.S. Cl. .................................... 205/777.5; 205/775
(58) Field of Search .............................. 205/775, 777.5

(56) References Cited

U.S. PATENT DOCUMENTS 5,582,697 A * 12/1996 Ikeda et al. ................. 204/403

FOREIGN PATENT DOCUMENTS

| JP | 2-310457 | 12/1990 |
|---|---|---|
| JP | 3-54447 | 3/1991 |
| JP | 5-340915 | 12/1993 |
| JP | 6-109693 | 4/1994 |
| JP | 8-320304 | 12/1996 |
| JP | 9-101280 | 4/1997 |
| JP | 9-201337 | 8/1997 |
| JP | 10-19832 | 1/1998 |

* cited by examiner

*Primary Examiner*—T. Tung
*Assistant Examiner*—Alex Noguerola
(74) *Attorney, Agent, or Firm*—McDermott, Will & Emery

(57) ABSTRACT

A method for determining the concentration of a substrate in a sample solution using an electrode system comprising a working electrode, a counter electrode, and a reaction layer which contains at least an oxidoreductase and an electron mediator and is formed on the electrode system to electrochemically measure a reduced amount of the electron mediator resulting from enzyme reaction in the reaction layer, wherein a third electrode is formed as an interfering substance detecting electrode. A current flowing between the counter electrode and the third electrode is measured which is taken as a positive error. Subsequently, voltage application between the counter electrode and the third electrode is released and a voltage for oxidizing the reduced form electron mediator is applied between the working electrode and the counter electrode to measure a current flowing between the two electrodes.

9 Claims, 2 Drawing Sheets

DEVICE AND METHOD FOR DETERMINING THE CONCENTRATION OF A SUBSTRATE

TECHNICAL FIELD

The present invention relates to a method for performing rapid and high accuracy determination of a substrate in a sample in a simplified manner.

BACKGROUND ART

As the method for quantitative analysis of sugars such as sucrose and glucose, polarimetry, colorimetry, reductiometry, and methods using a variety of chromatography have been developed. However, all of those methods have poor accuracy because of poor specificity to sugars. Of those methods, polarimetry is simple in manipulation but is largely affected by the temperature during operation. Therefore, polarimetry is not a suitable method for ordinary people to carry out determination of sugars at home or elsewhere in a simplified manner.

Apropos, various types of biosensor have been developed recently which use specific catalytic actions of enzymes.

In the following, a method of glucose determination will be described as one example of the method of substrate determination in a sample solution. A generally known electrochemical method of glucose determination is a method which uses glucose oxidase (EC1.1.3.4; hereinafter abbreviated to GOD) and an oxygen electrode or a hydrogen peroxide electrode (for instance, "Biosensor" ed. by Shuichi Suzuki, Kodansha).

GOD selectively oxidizes a substrate β-D-glucose to D-glucono-δ-lactone using oxygen as an electron mediator. Oxygen is reduced to hydrogen peroxide in the presence of oxygen in the course of oxidation reaction by GOD. A decreased amount of oxygen is measured by the oxygen electrode or, otherwise, an increased amount of hydrogen peroxide is measured by the hydrogen peroxide electrode. The decreased amount of oxygen or increased amount of hydrogen peroxide is proportional to the glucose content in the sample solution, so that glucose can be determined based on the decreased amount of oxygen or increased amount of hydrogen peroxide.

As can be speculated from the reaction process, this method has a drawback that the measurement result is largely affected by the oxygen concentration in the sample solution. Furthermore, measurement is impossible in the absence of oxygen in the sample solution.

Therefore, a novel type glucose sensor has been developed which does not use oxygen as the electron mediator but uses an organic compound or a metal complex including potassium ferricyanide, ferrocene derivatives, quinone derivatives, etc. as the electron mediator. This type of sensor oxidizes a reduced form electron mediator resulting from enzyme reaction on the electrode and determines glucose concentration contained in the sample solution based on the quantity of oxidation current. The use of such organic compound or metal complex as the electron mediator in place of oxygen enables formation of a reaction layer while exactly carrying a known amount of GOD and either of such electron mediators in a stabilized state. In this case, since the reaction layer can be integrated in an almost dry state with the electrode system, a disposable type glucose sensor based on this technology has been drawing much attention currently.

The disposable type glucose sensor facilitates measurement of glucose concentrations with a measurement device by simple introduction of a sample solution into the sensor detachably connected to the measurement device. Application of such technic is not limited only to glucose determination and can be extended to determination of other substrate contained in the sample solution.

Measurement using the sensor as described before can determine the substrate concentration based on a flowing oxidation current value resulting from oxidation of a reduced form electron mediator on a working electrode. However, when blood, a fruit juice or something like that is used as a sample, any easy-to-oxidize substance contained in the sample solution, such as ascorbic acid, uric acid, etc. is concurrently oxidized on the working electrode together with the reduced form electron mediator. Oxidation reaction of such easy-to-oxidize substance may sometimes affect the measurement result.

In addition, in the measurement using the sensor as mentioned above, a reaction producing hydrogen peroxide using dissolved oxygen as an electron mediator may proceed concurrently with the reduction of the carried electron mediator on the reaction layer. Furthermore, the hydrogen peroxide produced by the reaction reoxidizes the reduced form electron mediator. This may eventually produce a negative error in the measurement result due to the dissolved oxygen when the substrate concentration is to be measured based on the oxidation current of the reduced form electron mediator.

The above-mentioned method often applies a voltage between the working electrode and a counter electrode to detect liquid junction, namely, to detect supply of sample solution on the basis of an electrical change between the two electrodes prior to application of a voltage between the working electrode and the counter electrode in order to obtain a current response. At that time, it sometimes occurs that measurement starts before supply of sufficient amounts of sample solution to the electrode system due to a change in resistance value between the above-mentioned working electrode and the counter electrode, which may sometimes affect the measurement result. Induction of a change in the condition of an interface of the working electrode may also affect the measurement result.

Furthermore, a measurement method with a two-electrode system uses a counter electrode as a reference electrode. This causes a change in potential of the counter electrode as the standard in association with the oxidation-reduction reaction at the working electrode, which also affects the measurement result.

The object of the present invention is to eliminate inconveniences as described above and provide a method of determination facilitating accurate measurement of substrate concentration by removing influences of easy-to-oxidize substances.

Another object of the present invention is to provide a method of substrate determination with lesser variations in sensor response.

DISCLOSURE OF INVENTION

The present invention is a method for determining the concentration of a substrate in a sample solution using a biosensor comprising an electrically insulating base plate, an electrode system having a working electrode, a counter electrode and a third electrode to be used as an interfering substance detecting electrode, each being formed on the above-mentioned base plate, and a reaction layer which contains at least an oxidoreductase and an electron mediator and is formed on the electrode system omitting the third electrode, wherein the electron mediator is reduced by the generating electrons upon reaction between the substrate contained in the sample solution and the oxidoreductase to measure a reduced amount of the electron mediator electrochemically, the method being characterized by comprising the following steps:
(a) a step of applying a voltage between the counter electrode and the third electrode;
(b) a step of supplying the sample solution to the reaction layer;
(c) a step of detecting an electrical change between the counter electrode and the third electrode due to supply of the sample solution to the reaction layer;
(d) a step of measuring a current flowing between the counter electrode and the third electrode after the above-mentioned detecting step (c);
(e) a step of releasing voltage application between the counter electrode and the third electrode after the above-mentioned measuring step (d);
(f) a step of applying a voltage between the working electrode and the counter electrode; and
(g) a step of subsequently measuring a current flowing between the counter electrode and the working electrode.

The present invention also provides a method for determining the concentration of a substrate in a sample solution using a biosensor comprising an electrically insulating base plate, an electrode system having a working electrode, a counter electrode and a third electrode to be used as an interfering substance detecting electrode, each being formed on the above-mentioned base plate, a reaction layer which contains at least an oxidoreductase and an electron mediator and is formed on the electrode system omitting the third electrode, and a cover member forming a sample solution supply pathway to introduce a sample solution from a sample solution supply port into the above-mentioned reaction layer on the above-mentioned base plate, the third electrode being located upstream of the sample solution supply pathway from the reaction layer, wherein the electron mediator is reduced by the produced electrons upon reaction between the substrate contained in the sample solution and the oxidoreductase to measure a reduced amount of the electron mediator electrochemically, the method comprising the following steps:
(a) a step of applying a voltage between the counter electrode and the third electrode;
(b) a step of supplying the sample solution to the reaction layer;
(c) a step of detecting an electrical change between the counter electrode and the third electrode due to supply of the sample solution to the reaction layer;
(d) a step of measuring a current flowing between the counter electrode and the third electrode after the above-mentioned detecting step (c);
(e) a step of releasing voltage application between the counter electrode and the third electrode after the above-mentioned measuring step (d);
(f) a step of applying a voltage between the working electrode and the counter electrode; and
(g) a step of subsequently measuring a current flowing between the counter electrode and the working electrode.

For the method of determination in accordance with the present invention, the use of the third electrode as reference electrode is preferred. Namely, a voltage is also applied between the working electrode and the third electrode during the above-mentioned step (f).

When a biosensor with the cover member being integrally combined with the above-mentioned base plate is used, it is also preferable to provide a lecithin carrying layer on an exposed wall surface of the cover member to the sample solution supply pathway.

It is preferred that the above-mentioned reaction layer further contains a hydrophilic polymer.

BEST MODE FOR CARRYING OUT THE INVENTION

Figure 1:
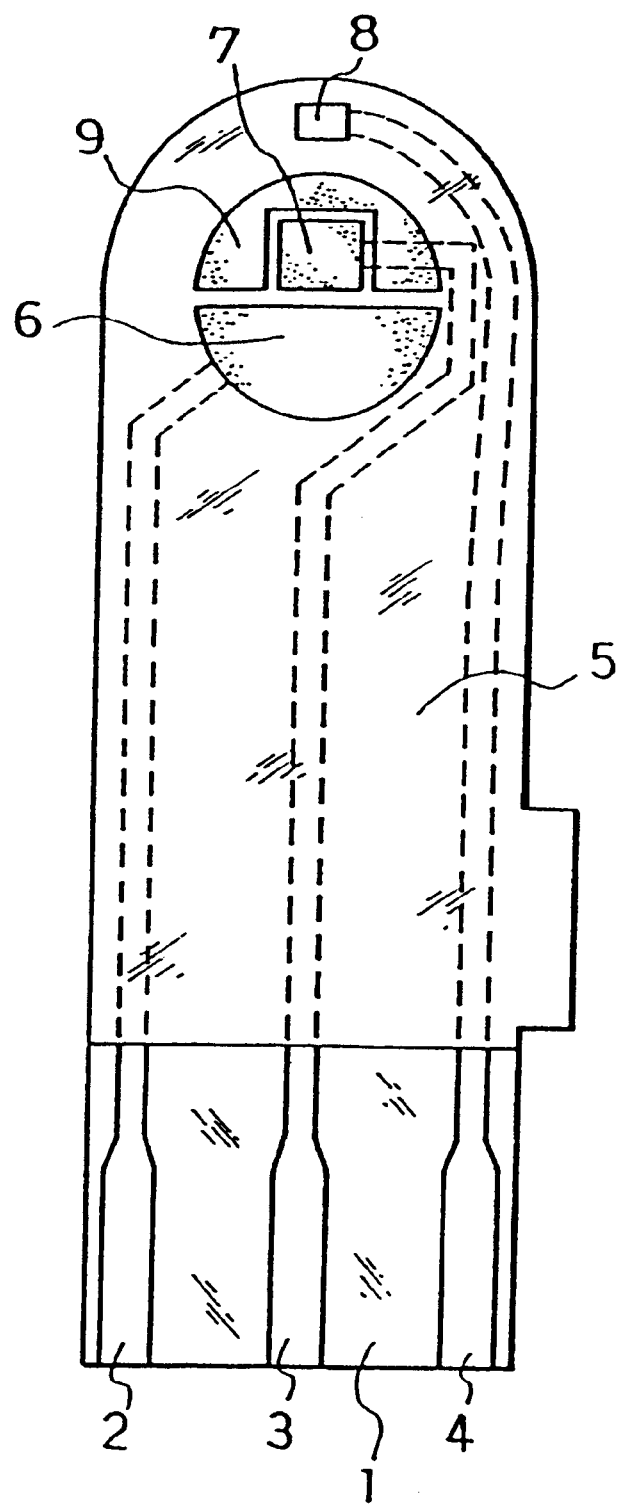
FIG. 1 is a plan view illustrating a glucose sensor in accordance with one example of the present invention from which the reaction layer has been omitted.

A structure of the biosensor to be used in the method of determination in accordance with the present invention will be described.

First, a first type biosensor will be described by way of FIG. 1.

In this sensor, a counter electrode 6, a working electrode 7 and a third electrode 8 are formed on an insulating base plate 1 made of polyethylene terephthalate, together with respective leads 2, 3 and 4 being electrically connected to them. A carbon layer 9 which is formed to facilitate production of reaction layer does not function as an electrode. A round reaction layer (not shown) containing an oxidoreductase and an electron mediator is formed on the counter electrode 6, the working electrode 7 and the carbon layer 9 omitting the third electrode 8. In the figure, numeral 5 represents an insulating layer.

Figure 2:
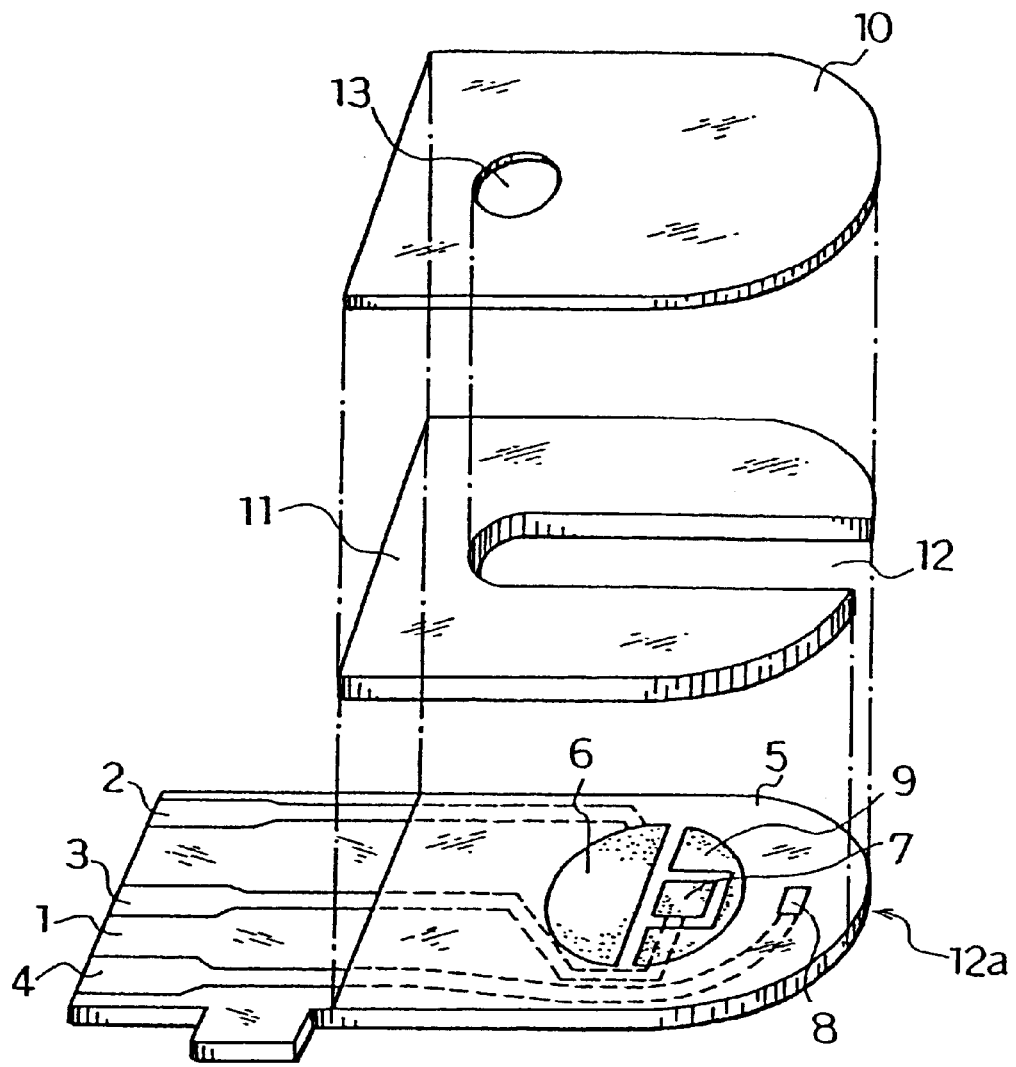
FIG. 2 is an exploded perspective view illustrating a glucose sensor in accordance with another example of the present invention from which the reaction layer has been omitted.

Next, a second type biosensor will be described by way of FIG. 2.

This sensor is a combination of the base plate 1 in FIG. 1 with a cover member comprising a cover 10 and a spacer 11. They are bonded to each other in a positional relationship as shown by the dotted chain line in FIG. 2 to form a sensor.

A slit 12 for forming the sample solution supply pathway is formed on the spacer 11, and an air vent 13 is formed on the cover 10. Laminating the cover 11 on the base plate 1 via the spacer 11 to bond them to each other results in formation of a cavity which serves as the sample solution supply pathway at the slit 12 on the spacer 11 by the base plate 1, spacer 11 and the cover 10. An end edge of this cavity communicates with the air vent 13.

In this biosensor, the working electrode 7 is located at a position closer to a sample solution supply port 12a (corresponding to an open edge of the slit 12) than the semilunar counter electrode 6, and the third electrode 8 is located at a position still closer to the sample solution supply port 12a than the working electrode 7. Each of these electrodes 6, 7 and 8 is exposed to the above-mentioned cavity.

In measuring the substrate concentration using the above-mentioned biosensor, an end portion of the sensor to which the leads 2, 3 and 4 are provided is set on a measurement device first, followed by application of a predetermined potential onto the third electrode 8 with reference to the counter electrode 6. With the potential being applied, a sample solution containing, for instance, ascorbic acid as an interfering substance is dropped on the reaction layer to dissolve the reaction layer in the sample solution.

Upon supply of the sample solution, a liquid supply detecting system starts to operate based on an electrical change between the counter electrode 6 and the third electrode 8 of the electrode system, which in turn starts a measurement timer. At that time, the potential is kept applied between the counter electrode 6 and the third electrode 8, and a current value between the counter electrode 6 and the third electrode 8 is measured when a certain time has passed after detection of supply of the sample solution. Since the reaction layer is omitted from the third electrode 8, it takes slight time until the reduced form electron mediator resulting from enzyme reaction reaches near the third electrode 8. Therefore, the above-mentioned current value must be derived from the oxidation reaction of the ascorbic acid contained as an interfering substance.

Next, the voltage application between the counter electrode 6 and the third electrode 8 is released.

Subsequently, a potential for oxidizing the above-mentioned reduced form electron mediator is applied onto the working electrode 7 with reference to the counter electrode 6 to measure a current value between the counter electrode 6 and the working electrode 7. This current is derived from the oxidation reactions of the reduced form electron mediator and the preexisting interfering substance ascorbic acid. In other words, the ascorbic acid produces a positive error in the measurement result. The above-mentioned current value between the counter electrode 6 and the third electrode 8 mainly reflects only the concentration of ascorbic acid, so that correction of the measurement result on the basis of this current value removes any influence of ascorbic acid, whereby an exact substrate concentration can be determined.

The second type sensor detects supply of the sample solution between the counter electrode 6 and the third electrode 8, so that the entire exposed area of the working electrode 7 is filled with the sample solution with security. As a result, supply of the sample solution can be determined more reliably.

In the following, the present invention will be described more specifically by way of examples.

EXAMPLE 1

A method of glucose determination will be described. The base plate shown in FIG. 1 was used for the base plate of a glucose sensor. The glucose sensor was produced as follows.

A silver paste was printed on the insulating base plate 1 made of polyethylene terephthalate by using screen printing to form the respective leads 2, 3 and 4. Next, a conductive carbon paste containing a resin binder was further printed on the base plate 1 to from the counter electrode 6, the working electrode 7, the third electrode 8 and the carbon layer 9. The counter electrode 6, the working electrode 7 and the third electrode 8 are electrically connected to the leads 2, 3 and 4, respectively.

Then, an insulating paste was printed on the base plate 1 to form the insulating layer 5. The insulating layer 5 covers a periphery of each of the counter electrode 6, the working electrode 7, the third electrode 8 and the carbon layer 9, whereby an exposed area of each of the counter electrode 6, the working electrode 7, the third electrode 8 and the carbon layer 9 is held constant. The insulating layer 5 partially covers the leads 2, 3 and 4.

Next, an aqueous solution of carboxymethyl cellulose (hereinafter abbreviated to CMC) was dropped on the counter electrode 6, working electrode 7 and carbon layer 9 omitting the third electrode 8 and dried to form a CMC layer.

Dropping an aqueous solution containing GOD as an enzyme and potassium ferricyanide as an electron mediator on the CMC layer once dissolves the CMC layer composed of a hydrophilic polymer, which is formed into a reaction layer by the subsequent drying process, with CMC being mixed with the enzyme and the other constituent. However, the absence of agitation, etc. results in incomplete mixing of the both, whereby the surface of the electrode system is covered with only CMC. In other words, because of no contact of the enzyme and the electron mediator with the surface of the electrode system, adsorption of protein onto the surface of the electrode system can be prevented.

In order to measure glucose concentrations using this sensor, an end portion of the sensor at which the leads 2, 3 and 4 are provided was set to a measurement device and a potential of 500 mV was applied onto the third electrode 8 with reference to the counter electrode 6. With the potential being kept applied, an aqueous glucose solution containing ascorbic acid as an interfering substance was dropped on the reaction layer as a sample solution at 30 $\mu$l. The reaction layer on the electrode system dissolved in the dropped sample solution.

Upon supply of the sample solution, a liquid supply detecting system started to operate based on an electrical change between the counter electrode 6 and the third electrode 8 of the electrode system. This started a measurement timer. At that time, the potential application is being continued between the counter electrode 6 and the third electrode 8, and after a lapse of a certain time from the detection of supply of the sample solution, a current between the counter electrode 6 and the third electrode 8 was measured. The current was derived from the oxidation reaction of the ascorbic acid contained as an interfering substance and had a proportional relationship with its concentration. After measurement of the current between the counter electrode 6 and the third electrode 8, the voltage application between the both electrodes was released.

As mentioned above, the reaction layer was not disposed on the third electrode 8. Therefore, it takes slight time until arrival of ferrocyanide ions resulting from enzyme reaction near the third electrode 8. Namely, the current value between the counter electrode 6 and the third electrode 8 during an interval until arrival of ferrocyanide ions mainly reflects only the concentration of ascorbic acid.

Furthermore, 25 seconds after detection of sample solution, 500 mV was applied onto the working electrode 7 with reference to the counter electrode 6 and a current value between the counter electrode 6 and the working electrode 7 was measured after 5 seconds.

Reaction of ferricyanide ions, glucose and GOD in the solution eventually oxidizes glucose to gluconolactone and reduces ferricyanide ions to ferrocyanide ions. The concentration of ferrocyanide ion is proportional to the glucose concentration. A current between the counter electrode 6 and the working electrode 7 after 30 seconds of detection of the sample solution is derived from the oxidation reactions of ferrocyanide ions and preexisting ascorbic acid. This means that ascorbic acid produces a positive error in the measurement result. However, as described before, the current value between the counter electrode 6 and the third electrode 8 mainly reflects only the concentration of ascorbic acid. Therefore, correction of the measurement result based on that result can remove any effects of ascorbic acid thereby enabling determination of accurate glucose concentration.

EXAMPLE 2

The electrodes 6, 7, 8 and carbon layer 9 were formed on the base plate 1 in the same manner as in Example 1. Next, an aqueous CMC solution was dropped on the counter electrode 6, working electrode 7 and carbon layer 9 while omitting the third electrode 8 and dried to form the CMC layer, on which an aqueous solution containing GOD as an enzyme and potassium ferricyanide as an electron mediator was further dropped and dried to form the reaction layer.

Next, for further smoothing supply of the sample solution to the reaction layer, an organic solvent solution of lecithin, such as toluene solution, for example, was spread from the sample solution supply port toward the reaction layer and dried to form a lecithin layer on the reaction layer. Next, the cover 10 and the spacer 11 were bonded to the base plate 1 in a positional relationship as shown by the dotted chain line in FIG. 2 to form a glucose sensor.

The sensor was set on a measurement device and a potential of 500 mV was applied onto the third electrode 8 with reference to the counter electrode 6. With the potential kept applied, an aqueous glucose solution containing ascorbic acid as an interfering substance was supplied through the sample solution supply port 12a at 3 $\mu$l as a sample solution. The sample solution reached the air vent 13 by passing through the sample solution supply pathway and dissolved the reaction layer on the electrode system.

Upon supply of the sample solution, a liquid supply detecting system started to operate based on an electrical change between the counter electrode 6 and the third electrode 8 of the electrode system. This started a measurement timer. At that time, the potential application is being continued between the counter-electrode 6 and the third electrode 8, and after a lapse of a certain time from the detection of supply of the sample solution, a current between the counter electrode 6 and the third electrode 8 was measured. The current was derived from the oxidation reaction of the ascorbic acid contained as an interfering substance and had a proportional relationship with its concentration. After measurement of the current between the counter electrode 6 and the third electrode 8, the voltage application between the two electrodes was released.

As mentioned above, the reaction layer was not disposed on the third electrode 8. Therefore, it takes slight time until arrival of ferrocyanide ions resulting from enzyme reaction near the third electrode 8. Namely, the current value between the counter electrode 6 and the third electrode 8 during an interval until arrival of ferrocyanide ion mainly reflects only the concentration of ascorbic acid.

Furthermore, 25 seconds after detection of the sample solution, 500 mV was applied onto the working electrode 7 with reference to the counter electrode 6 and a current value between the counter electrode 6 and the working electrode 7 was measured after 5 seconds.

Reaction of ferricyanide ions, glucose and GOD in the solution eventually oxidizes glucose to gluconolactone and reduces ferricyanide ions to ferrocyanide ions. The concentration of ferrocyanide ion is proportional to the glucose concentration. A current between the counter electrode 6 and the working electrode 7 after 30 seconds of detection of the sample solution is derived from the oxidation reactions of ferrocyanide ions and preexisting ascorbic acid. This means that ascorbic acid produces a positive error in the measurement result. However, as described before, the current value between the counter electrode 6 and the third electrode 8 mainly reflects only the concentration of ascorbic acid. Therefore, correction of the measurement result based on that result can remove any effects of ascorbic acid thereby enabling determination of accurate glucose concentration.

In the present example, due to detection of supply of the sample solution between the counter electrode 6 and the third electrode 8, the entire exposed portion of the working electrode 7 is filled with the sample solution with security. This enables still more reliable determination of supply of the sample solution.

EXAMPLE 3

A glucose sensor was produced in the same manner as in Example 2.

The sensor was set on a measurement device and a potential of 500 mV was applied onto the third electrode 8 with reference to the counter electrode 6. With the potential kept applied, an aqueous glucose solution containing ascorbic acid as an interfering substance was supplied through the sample solution supply port 12a at 3 $\mu$l as a sample solution. The sample solution reached the air vent 13 by passing through the sample solution supply pathway and dissolved the reaction layer on the electrode system.

Upon supply of the sample solution, a liquid supply detecting system started to operate based on an electrical change between the counter electrode 6 and the third electrode 8 of the electrode system, which then started a measurement timer. At that time, the potential application is being continued between the counter electrode 6 and the third electrode 8, and after a lapse of a certain time from the detection of supply of the sample solution, a current between the counter electrode 6 and the third electrode 8 was measured. The current was derived from the oxidation reaction of the ascorbic acid contained as an interfering substance and had a proportional relationship with its concentration. After measurement of the current between the counter electrode 6 and the third electrode 8, the voltage application between the two electrodes was released.

As mentioned above, the reaction layer was not disposed on the third electrode 8. Therefore, it takes slight time until arrival of ferrocyanide ions resulting from enzyme reaction near the third electrode 8. Namely, the current value between the counter electrode 6 and the third electrode 8 during an interval until arrival of ferrocyanide ions mainly reflects only the concentration of ascorbic acid.

Furthermore, 25 seconds after detection of the sample solution, 500 mV was applied onto the working electrode 7 with reference to the third electrode 8 and a current value between the counter electrode 6 and the working electrode 7 was measured after 5 seconds.

Reaction of ferricyanide ions, glucose and GOD in the solution eventually oxidizes glucose to gluconolactone and reduces ferricyanide ions to ferrocyanide ions. The concentration of ferrocyanide ion is proportional to the glucose concentration. A current between the counter electrode 6 and the working electrode 7 after 30 seconds of detection of the sample solution is derived from the oxidation reactions of ferrocyanide ions and preexisting ascorbic acid. This means that ascorbic acid produces a positive error in the measurement result. However, as described before, the current value between the counter electrode 6 and the third electrode 8 mainly reflects only the concentration of ascorbic acid. Therefore, correction of the measurement result based on that result can remove any effects of ascorbic acid thereby enabling determination of accurate glucose concentration.

Additional measurement of a potential of the third electrode 8 during potential application onto the working electrode 7 with reference to a silver/silver chloride electrode demonstrated almost no change in potential of the third electrode 8 although oxidation reaction occurred at the working electrode 7. Variations in sensor response were also decreased compared to the conventional method which detects liquid junction based on a change in resistance between the working electrode and the counter electrode.

EXAMPLE 4

In the same manner as in Example 2, the reaction layer was formed on the counter electrode 6, working electrode 7 and carbon layer 9 while omitting the third electrode 8.

Next, an organic solvent solution of lecithin such as toluene solution, for example, was spread on a groove formed on the cover member for forming the sample solution supply pathway and dried, thereby to form the lecithin layer for the purpose of still more smoothing supply of the sample solution to the reaction layer. Then, the cover 10 and the spacer 11 were bonded to the base plate 1 in a positional relationship as shown by the dotted chain line in FIG. 2, which gave a glucose sensor.

Positioning the lecithin layer from the reaction layer over the third electrode 8 may sometimes increase variations in sensor response characteristics due to a change of the surface of the third electrode by the lecithin layer. Positioning the lecithin layer on the cover member side as shown above resulted in a decrease in such variations, and the response characteristics improved.

EXAMPLE 5

A glucose sensor was produced completely in the same manner as in Example 2 except for omission of the CMC layer from the reaction layer.

And, the result of measurement in the same manner as in Example 2 showed dependency on the ascorbic acid and glucose concentrations despite increased variations in sensor response as compared to the case of including the CMC layer.

EXAMPLE 6

A glucose sensor was produced in the same manner as in Example 4.

The sensor was set on a measurement device and a potential of −1,300 mV was applied onto the third electrode 8 with reference to the counter electrode 6. With the potential kept applied, an air saturated aqueous glucose solution was supplied through the sample solution supply port 12a at 3 µl as a sample solution. The sample solution reached the air vent 13 by passing through the sample solution supply pathway and dissolved the reaction layer on the electrode system.

Upon supply of the sample solution, a liquid supply detecting system started to operate based on an electrical change between the counter electrode 6 and the third electrode 8 of the electrode system, which started a measurement timer. At that time, the potential application is being continued between the counter electrode 6 and the third electrode 8, and after a lapse of a certain time from the detection of supply of the sample solution, a current between the counter electrode 6 and the third electrode 8 was measured. The current was derived from the reduction reaction of the dissolved oxygen. When a glucose solution degassed with argon was supplied, the reduction current decreased drastically. After measurement of the current between the counter electrode 6 and the third electrode 8, the voltage application between the two electrodes was released.

As mentioned above, the reaction layer was not disposed on the third electrode 8. Therefore, it takes slight time until arrival of ferricyanide ions in the reaction layer near the third electrode 8. Namely, the current value between the counter electrode 6 and the third electrode 8 during an interval until arrival of ferricyanide ions mainly reflects only the concentration of dissolved oxygen.

Furthermore, 25 seconds after detection of the sample solution, 500 mV was applied onto the working electrode 7 with reference to the third electrode 8 and a current value between the counter electrode 6 and the working electrode 7 was measured after 5 seconds.

Reaction of ferricyanide ions, glucose and GOD in the solution eventually oxidizes glucose to gluconolactone, and reduction of ferricyanide ions to ferrocyanide ions occurs with this oxidation reaction.

On the other hand, a reaction proceeds at the same time as a competitive reaction where dissolved oxygen is reduced to hydrogen peroxide as the glucose is oxidized to gluconolactone due to the action of the dissolved oxygen in the sample solution as an electron mediator. Hydrogen peroxide generating by this reaction reoxidizes ferrocyanide ions to ferricyanide ions. Therefore, if glucose concentration is to be measured based on an oxidation current of ferrocyanide ion, such dissolved oxygen can produce a negative error in the measurement result.

However, as mentioned before, the current value between the counter electrode 6 and the third electrode 8 mainly reflects only the concentration of dissolved oxygen. Therefore, correction of the measurement result based on that result can remove any effects of dissolved oxygen thereby enabling determination of accurate glucose concentration.

EXAMPLE 7

A glucose sensor was produced in the same manner as in Example 4.

The sensor was set on a measurement device and a potential of 500 mV was applied onto the third electrode 8 with reference to the counter electrode 6. With the potential kept applied, an aqueous glucose solution containing ascorbic acid as an interfering substance was supplied through the sample solution supply port 12a at 3 µl as a sample solution. The sample solution reached the air vent 13 by passing through the sample solution supply pathway and dissolved the reaction layer on the electrode system.

Upon supply of the sample solution, a liquid supply detecting system started to operate based on an electrical change between the counter electrode 6 and the third electrode 8 of the electrode system, which started a measurement timer. At that time, the potential application is being continued between the counter electrode 6 and the third electrode 8. Two seconds after detection of supply of the sample solution, the potential to be applied onto the third electrode 8 was changed to −1,300 mV. The current between the counter electrode 6 and the third electrode 8 was measured at two time points immediately before and 3 seconds after the potential change to −1,300 mV. The current immediately before the potential change is mainly dependent on the concentration of ascorbic acid. On the other hand, the current 3 seconds after the potential change to −1,300 mV is mainly dependent on the concentration of dissolved oxygen in the sample solution.

After measurements of the current between the counter electrode 6 and the third electrode 8 after 2 and 5 seconds of supply of the sample solution, the voltage application between the two electrodes was released.

Twenty-five seconds after detection of the sample solution, 500 mV was further applied onto the working electrode 7 with reference to the third electrode 8 and the current between the counter electrode 6 and the working electrode 7 was measured after 5 seconds.

As described above, the current value between the counter electrode 6 and the third electrode 8 mainly reflects concentrations of ascorbic acid and dissolved oxygen. Therefore, concentrations of those two substances can be determined based on that current value. Therefore, correction of the measurement result based on that result can remove any effects of ascorbic acid and dissolved oxygen thereby enabling determination of accurate glucose concentration.

In the foregoing examples, although the potential to be applied onto the third electrode 8 for sensing supply of the sample solution to detect ascorbic acid or dissolved oxygen was 500 mV or −1,300 mV, the present invention is not limited to those potential values. Moreover, although a potential of 500 mV was applied onto the working electrode 7 to obtain a response current, the present invention is not limited to this potential value and any potential may be used if it can oxidize the reduced form electron mediator resulting from a series of reaction. The time point to measure the current value is also not limited to those used in the foregoing examples.

In the foregoing examples, although carboxymethyl cellulose was used as the hydrophilic polymer, a variety of hydrophilic polymers can be used for forming the hydrophilic polymer layer. Exemplary hydrophilic polymers include hydroxyethyl cellulose, hydroxypropyl cellulose, methyl cellulose, ethyl cellulose, ethylhydroxyethyl cellulose, carboxymethylethyl cellulose, polyvinyl pyrrolidone, polyvinyl alcohol, polyamino acid such as polylysin, polystyrene sulfonate, gelatin and its derivatives, polyacrylic acid and its salts, polymethacrylic acid and its salts, starch and its derivatives, and a polymer of maleic anhydride or a maleate. Of them, carboxymethyl cellulose, hydroxyethyl cellulose and hydroxypropyl cellulose are preferred.

The oxidoreductase to be contained in the reaction layer is selected depending on the substrate contained in the sample solution. Exemplary oxidoreductases include fructose dehydrogenase, glucose oxidase, alcohol oxidase, lactate oxidase, cholesterol oxidase, xanthine oxidase, and amino-acid oxidase.

As the electron mediator, potassium ferricyanide, p-benzoquinone, phenazine methosulfate, methylene blue, and ferrocene derivatives may be exemplified. These electron mediators may be used singly or in combination of two or more.

The above-exemplified enzymes and electron mediators may be dissolved in the sample solution or may be prevented from dissolving in the sample solution by fixing the reaction layer onto the base plate and so on. When the enzyme and the electron mediator are to be fixed, the reaction layer preferably contains the hydrophilic polymer.

In the foregoing examples, specific electrode systems were shown, but the present invention is not limited to those electrode systems with respect to the shape of the electrode and location of the electrodes and leads.

In the foregoing examples, although carbon was used as the material of the third electrode, the present invention is not limited to carbon electrode and those made of other conductive material or a silver/silver chloride electrode can also be used.

Industrial Applicability

As discussed above, the present invention enables substrate determination of high reliability.

What is claimed is:

1. A method for determining the concentration of a substrate in a sample solution using a biosensor comprising an electrically insulating base plate, an electrode system having a working electrode, a counter electrode and a third electrode to be used as an interfering substance detecting electrode, each being formed on said base plate, and a reaction layer which contains at least an oxidoreductase and an electron mediator and is formed on the electrode system omitting the third electrode, wherein said electron mediator is reduced by the produced electrons upon reaction between the substrate contained in the sample solution and the oxidoreductase to measure a reduced amount of said electron mediator electrochemically, said method being characterized by comprising:
(a) a step of applying a voltage between the counter electrode and the third electrode;
(b) a step of supplying the sample solution to the reaction layer;
(c) a step of detecting an electrical change between the counter electrode and the third electrode due to supply of the sample solution to the reaction layer;
(d) a step of measuring a current flowing between the counter electrode and the third electrode after said detecting step (c);
(e) a step of releasing voltage application between the counter electrode and the third electrode after said measuring step (d);
(f) a step of applying a voltage between the working electrode and the counter electrode; and
(g) a step of subsequently measuring a current flowing between the counter electrode and the working electrode.

2. The method of claim 1, wherein said step (f) also applies a voltage between the working electrode and the third electrode.

3. The method of claim 1, wherein said biosensor further contains a hydrophilic polymer in said reaction layer.

4. The method of claim 1, wherein the measurement of the current between the counter electrode and the third electrode is performed after a predetermined amount of time after the detection of the electrical change between the counter electrode and the third electrode in step (c).

5. A method for determining the concentration of a substrate in a sample solution using a biosensor comprising an electrically insulating base plate, an electrode system having a working electrode, a counter electrode and a third electrode to be used as an interfering substance detecting electrode, each being formed on said base plate, a reaction layer which contains at least an oxidoreductase and an electron mediator and is formed on said electrode system omitting the third electrode, and a cover member forming a sample solution supply pathway to introduce a sample solution from a sample solution supply port into said reaction layer on said base plate, said third electrode being located upstream of said sample solution supply pathway from said reaction layer, wherein said electron mediator is reduced by the produced electrons upon reaction between the substrate contained in the sample solution and the oxidoreductase to measure a reduced amount of said electron mediator electrochemically, said method being characterized by comprising:
(a) a step of applying a voltage between the counter electrode and the third electrode;
(b) a step of supplying the sample solution to the reaction layer;
(c) a step of detecting an electrical change between the counter electrode and the third electrode due to supply of the sample solution to the reaction layer;

(d) a step of measuring a current flowing between the counter electrode and the third electrode after said detecting step (c);

(e) a step of releasing voltage application between the counter electrode and the third electrode after said measuring step (d);

(f) a step of applying a voltage between the working electrode and the counter electrode; and (g) a step of subsequently measuring a current flowing between the counter electrode and the working electrode.

6. The method of claim 5, wherein said step (f) also applies a voltage between the working electrode and the third electrode.

7. The method of claim 5, wherein said biosensor is disposed with a layer essentially composed of lecithin on an exposed surface of the sample solution supply pathway of said cover member.

8. The method of claim 5, wherein said biosensor further contains a hydrophilic polymer in said reaction layer.

9. The method of claim 5, wherein the measurement of the current between the counter electrode and the third electrode is performed after a predetermined amount of time after the detection of the electrical change between the counter electrode and the third electrode in step (c).

* * * * *